(12) United States Patent
Fronabarger et al.

(10) Patent No.: US 10,464,908 B2
(45) Date of Patent: Nov. 5, 2019

(54) PURIFICATION OF FLOW SODIUM 5-NITROTETRAZOLATE SOLUTIONS WITH COPPER MODIFIED CATION EXCHANGE RESIN

(71) Applicant: Pacific Scientific Energetic Materials Company, Chandler, AZ (US)

(72) Inventors: John W. Fronabarger, Sun Lakes, AZ (US); Jason B. Pattison, Phoenix, AZ (US); Lily F. W. Walsh, Phoenix, AZ (US)

(73) Assignee: Pacific Scientific Energetic Materials Company, Chandler, AZ (US)

(*) Notice: Subject to any disclaimer, the term of this patent is extended or adjusted under 35 U.S.C. 154(b) by 0 days.

(21) Appl. No.: 15/698,095

(22) Filed: Sep. 7, 2017

(65) Prior Publication Data

US 2018/0111909 A1  Apr. 26, 2018

Related U.S. Application Data

(60) Provisional application No. 62/384,511, filed on Sep. 7, 2016.

(51) Int. Cl.
| | |
|---|---|
| *C07D 257/06* | (2006.01) |
| *B01J 39/05* | (2017.01) |
| *B01J 39/07* | (2017.01) |
| *B01J 39/20* | (2006.01) |
| *B01J 47/016* | (2017.01) |

(52) U.S. Cl.
CPC ............ *C07D 257/06* (2013.01); *B01J 39/05* (2017.01); *B01J 39/07* (2017.01); *B01J 39/20* (2013.01); *B01J 47/016* (2017.01)

(58) Field of Classification Search
CPC ......... C07D 257/06; B01J 39/05; B01J 39/07; B01J 39/20
USPC ............................................................ 521/38
See application file for complete search history.

(56) References Cited

U.S. PATENT DOCUMENTS

| | | | |
|---|---|---|---|
| 2,066,954 | A | 1/1937 | Von Herz et al. |
| 3,054,800 | A | 9/1962 | Burchfield et al. |
| 3,111,524 | A | 11/1963 | Wiley et al. |
| 4,093,623 | A * | 6/1978 | Gilligan .................. C06B 41/00 548/109 |
| 4,094,879 | A | 6/1978 | Bates et al. |
| 4,552,598 | A | 11/1985 | Lee et al. |
| 5,376,240 | A * | 12/1994 | Kaczur .................. C02F 1/4676 205/617 |
| 6,375,871 | B1 | 4/2002 | Bentsen et al. |
| 6,437,104 | B1 | 8/2002 | Nickel et al. |
| 6,469,147 | B2 | 10/2002 | Nickel et al. |
| 6,495,016 | B1 | 12/2002 | Nawracala et al. |
| 6,648,015 | B1 | 11/2003 | Chow et al. |
| 6,737,026 | B1 | 5/2004 | Guan et al. |
| 7,253,288 | B2 | 8/2007 | Renz et al. |
| 9,670,168 | B2 | 6/2017 | Bragg et al. |
| 9,718,791 | B2 * | 8/2017 | Bragg ...................... B01J 19/24 |
| 2007/0161801 | A1 | 7/2007 | Renz et al. |
| 2014/0206885 | A1 | 7/2014 | Fronabarger et al. |
| 2015/0361057 | A1 | 12/2015 | Bottaro et al. |
| 2016/0207892 | A1* | 7/2016 | Bragg ...................... B01J 19/24 |

FOREIGN PATENT DOCUMENTS

| | | | |
|---|---|---|---|
| CN | 101164433 | A * | 4/2008 |
| DE | 562511 | | 11/1932 |
| EP | 1786789 | | 11/2010 |
| EP | 2948435 | | 12/2015 |
| JP | 4831515 | | 9/2011 |
| WO | 2001059013 | | 8/2001 |
| WO | 2003037502 | | 5/2003 |
| WO | 2006029193 | | 3/2006 |
| WO | 2014116654 | | 7/2014 |
| WO | 2016115564 | | 7/2016 |

OTHER PUBLICATIONS

Ahn et al., "Centrifugal gas-liquid separation under low gravity conditions", Lab-On-A-Chip vol. 4, Jun. 2000, pp. 121-129.
Amon et al., "Direct Methanol Micro Fuel Cell for Powering Micro Sensors", http://www.drapa.mil/mto/mpg/summaries/2003.sub--1/cmu.html, 2003, 3 pages.
Brooks et al., "Component development for a microchannel in situ propellant production system", AIChE 2002 Spring National Meeting, Mar. 10-14, 2002, 11 pages.
Dimian et al., Integrated design and simulation of chemical processes, Chemical-Aided Chemical Engineering, vol. 35, 2nd Edition, 2014, 12 pages.
Doyle et al., "Alkyl nitrite-metal halide deamination reactions. 2. Substitutive deamination of arylamines by alkyl nitrites and copper(II) halides. A direct and remarkably efficient conversion of arylamines to aryl halides", J. Org. Chem., vol. 42, No. 14, 1977, pp. 2426-2431.
Fortt et al., "Continuous-Flow Generation of Anhydrous Diazonium Species: Monolithic Microfluidic Reactors for the Chemistry of Unstable Intermediates", Org. Proc. Res. Dev., vol. 7, No. 5, 2003, pp. 762-768.
Galli, "Substituent effects on the Sandmeyer reaction. Quantitative evidence for rate-determining electron transfer", Journal of the Chemical Society, Perkin Transactions 2, 1984, pp. 897-902.
Gunther et al., "Transport and reaction in microscale segmented gas-liquid flow", Lab-on-a-chip, vol. 4, 2004, pp. 278-286.
Gutmann et al., "Synthesis of 5-Substituted 1 H-Tetrazoles from Nitriles and Hydrazoic Acid by Using a Safe and Scalable High-Temperature Microreactor Approach", Angewandte Chemie International Edition, vol. 49, 2010, pp. 7101-7105.
Kanno et al., "Microreactor: New Device for Organic and Enzymatic Synthesis", Journal of Synthetic Organic Chemistry, vol. 60, No. 7, Jan. 22, 2010, pp. 701-707.

(Continued)

*Primary Examiner* — Michael Bernshteyn
(74) *Attorney, Agent, or Firm* — Kilpatrick Townsend & Stockton LLP

(57) ABSTRACT

Described are methods for purifying a 5-nitrotetrazolate solution with a copper(II) modified cation exchange resin. The method can be performed as a stand-alone system or as a system integrated into a continuous flow reactor.

6 Claims, 2 Drawing Sheets

(56) References Cited

OTHER PUBLICATIONS

Klapoetke et al., "Preparation of High Purity Sodium 5-Nitrotetrazolate (NaNT): An Essential Precursor to the Environmentally Acceptable Primary Explosive, DBX-1", Z. Anorg. Allg. Chem, vol. 639, (5), Mar. 15, 2013, pp. 681-688.
Klapotke et al., "Simple, Nitrogen-Rich, Energetic Salts of 5-Nitrotetrazole", Inorg. Chem., vol. 47, No. 13, Jun. 7, 2008, pp. 6014-6027.
Kralj, "Preparation of Sodium Nitrotetrazolate using Microreactor Technology", American Institute of Aeronautics and Astronautics, Jul. 10-13, 2005, 6 pages.
Lowe et al., "Flow chemistry: Imidazole-based ionic liquid syntheses in micro-scale", Chemical Engineering Journal, 163 (3), 2010, pp. 429-437.
Okamoto, "Are Microreactors Useful for Organic Synthesis", Journal of Synthetic Organic Chemistry, vol. 57, No. 9, 1999, pp. 805-812.
Tegrotenhuis et al., "Normal Gravity Testing of a Microchannel Phase Separator for Insitu Resource Utilization", NASA/Cr-2001-210955, Jun. 2001, 22 pages.
Wootton et al., "On-chip generation and reaction of unstable intermediates—monolithic nanoreactors for diazonium chemistry: Azo dyes", Lab Chip 2(1),5-7., Jan. 22, 2002.
International Preliminary Report on Patentability, PCT Application No. PCT/US2017/050481, dated Mar. 21, 2019, 7 pages.

\* cited by examiner

US 10,464,908 B2

PURIFICATION OF FLOW SODIUM 5-NITROTETRAZOLATE SOLUTIONS WITH COPPER MODIFIED CATION EXCHANGE RESIN

CROSS-REFERENCE TO RELATED APPLICATIONS

This application claims the benefit of U.S. Provisional Application Ser. No. 62/384,511, filed Sep. 7, 2016, titled "Purification of Flow Sodium 5-nitrotetrazolate solutions with Copper Modified Cation Exchange Resin," the entire contents of which are hereby incorporated by reference.

FIELD OF THE INVENTION

The present invention is directed to the field of substituted tetrazole synthesis and manufacture. More particularly, the present invention is directed to processes for preparing substituted tetrazoles and tetrazolate salts, such as sodium 5-nitrotetrazolate, utilizing flow chemistry techniques. The use of the present technique results in less hazardous, more efficient large scale manufacturing processes.

The present invention is directed to the field of purification of sodium 5-nitrotetrazolate ("NaNT") for the production of the primary explosive DBX-1, as described in U.S. Pat. Nos. 7,833,330, 8,163,786, and 9,278,984. More particularly, the present invention is directed to the processes of purifying NaNT solutions by passing through a filter bed loaded with copper modified cation exchange resin. The use of the present technique results in less hazardous, more efficient large scale manufacturing processes.

BACKGROUND

Sodium 5-nitrotetrazolate is currently generated by both batch (U.S. Pat. No. 4,093,623) and continuous flow (U.S. Pat. Nos. 7,253,288 and 9,718,791) processes. However, the product solutions generated by both of these processes contain various impurities at concentrations that render the solutions incapable of DBX-1 formation without additional purification steps.

Analytical investigations of both batch and flow process product solutions have detected multiple organic impurities including 1H-tetrazole, 5,5'-bitetrazole, bitetrazoleamine, 5-nitraminotetrazole, tetrazolone, 5-azidotetrazole and DTET, as well as several unidentified compounds. High concentrations of nitrite, nitrate, and other anionic species can also interfere with DBX-1 production—a problem in NaNT solutions generated by some techniques. Currently, removal of detrimental impurities is accomplished by time consuming, laborious, and hazardous techniques requiring precipitation, extraction, titration, heating, fine filtration and/or other inefficient steps. These techniques are prohibitive for high volume production of DBX-1.

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Certain embodiments of the present invention describe a method for purifying a 5-nitrotetrazolate solution with a copper(II) modified cation exchange resin. In some embodiments, the method is performed as a stand-alone system and, in others, the method is performed as a system integrated into a continuous flow reactor.

In some embodiments, impurities were removed from a sodium 5-nitrotetrazolate solution when exposed to the cation exchange resin, which had previously been modified with copper(II) chloride dihydrate. The raw solution was passed through a glass column loaded with copper modified cation exchange resin, collected and subsequently used to successfully generate DBX-1. Concentrations of 1H-tetrazole, bitetrazoleamine, and 5-nitraminotetrazole were determined in pre- and post-purified NaNT solutions by HPLC. Significant decreases in the concentration of these impurities were observed after exposure to the copper modified resin.

The method may further include treating the 5-nitrotetrazolate solution with an acid solution or a resin bound acid prior to treating the 5-nitrotetrazolate solution with the copper(II) modified cation exchange resin. In certain embodiments, this method for removing excess nitrite remaining in some NaNT solutions produced by flow technology was developed by using a cation exchange resin which had been converted to the acid form. A raw 5-nitrotetrazolate solution that was initially ineffective for DBX-1 formation was sufficiently purified to a level capable of generating DBX-1.

Additionally, the method may include raising a pH of the 5-nitrotetrazolate solution after treating with the acid solution or the resin bound acid. The method may yet further include rinsing the copper(II) modified cation exchange resin with at least one of a copper(II) salt solution and deionized water after treating the 5-nitrotetrazolate solution.

Certain embodiments of the present invention comprise a copper(II) modified cation exchange resin, wherein the resin reduces a concentration of at least excess tetrazole in a 5-nitrotetrazolate solution when the 5-nitrotetrazolate solution is treated with the resin. In some embodiments, the concentration of the excess tetrazole in the 5-nitrotetrazolate solution is sufficiently low after treatment with the resin so as not to interfere when the 5-nitrotetrazolate solution is used to produce DBX-1. The capacity of the resin to reduce the concentration of the excess tetrazole in the 5-nitrotetrazolate solution may be restored after the capacity has been exceeded by rinsing with at least one of a copper(II) salt solution and deionized water.

Certain embodiments of the present invention comprise an acid form of an acid cation exchange resin, wherein the acid form of the resin reduces a concentration of at least excess nitrite in a 5-nitrotetrazolate solution when the 5-nitrotetrazolate solution is treated with the acid form of the resin.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1:
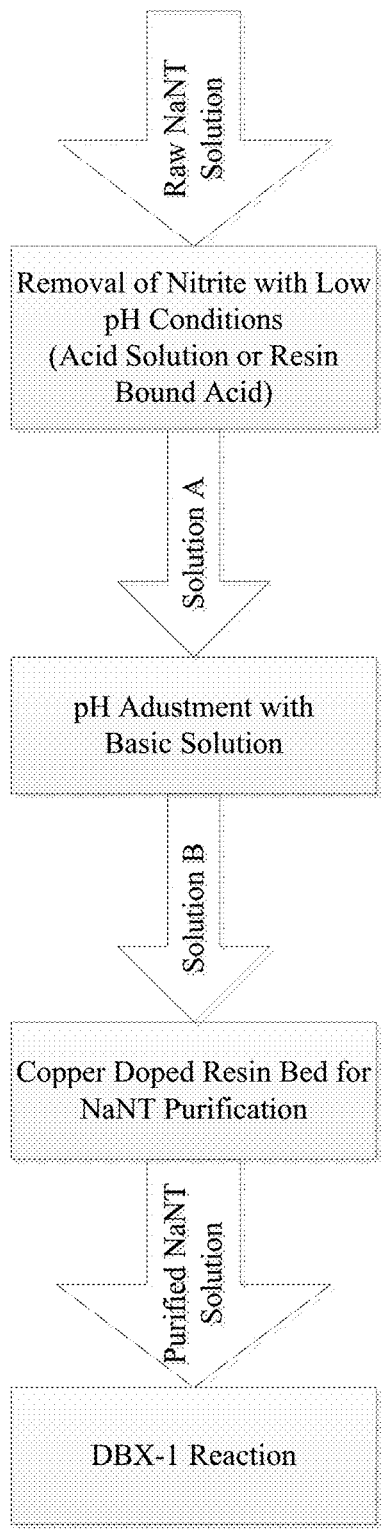
FIG. 1 is a flow diagram of a method used for purification of NaNT, according to certain embodiments of the present invention.

According to certain embodiments, as best illustrated in FIG. 1, a process has been developed to prepare high purity NaNT solution by elution through a bed of copper modified cation exchange resin at ambient temperature. The process produces NaNT solution of suitable purity to subsequently produce DBX-1 by batch reaction.

Figure 2:
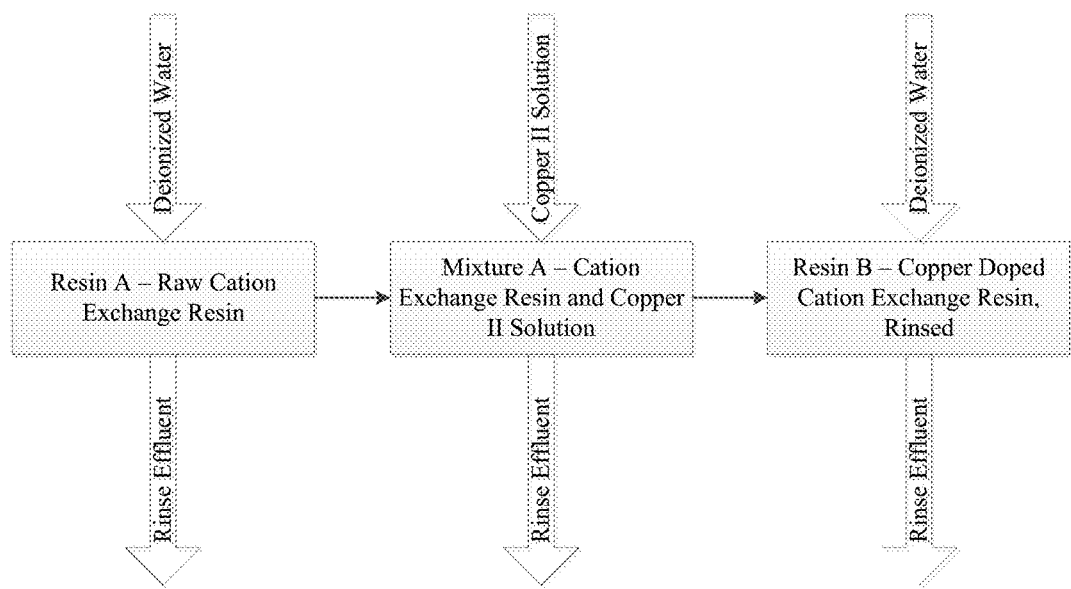
FIG. 2 is a flow diagram of a method used for preparation of a copper(II) modified cation exchange resin, according to certain embodiments of the present invention.

A raw NaNT solution for purification by the procedure as best illustrated in FIG. 1 may be obtained from batch, continuous flow, or other processes. NaNT solutions generated by the flow process described in U.S. Pat. No. 9,718,791, the entire contents of which is incorporated herein by reference, may contain residual nitrite from the manufacturing process. The raw NaNT solution is treated with acidic solution or resin bound acid to remove excess nitrite to produce Solution A. Appropriate acids include hydrochloric acid, nitric acid, sulfuric acid, perchloric acid, or other mineral or organic acids. Resin bound acid may also be used. Resin bound acids may be prepared from strong acid cation resins such as Dowex Marathon C, and converted to the acid form by immersion in a suitable acid solution, as best illustrated in FIG. 2. Acid solutions used for this purpose may consist of 1%-15% hydrochloric acid, nitric acid, sulfuric acid, perchloric acid, or other strong acids in aqueous solution. The acid solution may be 8% hydrochloric acid in aqueous solution. The mole ratio of nitrite to resin active sites may range from 1:1 to 0.01:1. The mole ratio of nitrite to resin active sites can be 0.55:1.

The pH of Solution A (FIG. 1) may be adjusted to between 1 and 10 with appropriate acid or base, including hydrochloric, nitric, or perchloric acid and sodium hydroxide, potassium hydroxide, sodium carbonate, potassium carbonate, sodium bicarbonate or potassium bicarbonate to generate Solution B (FIG. 1). The pH of Solution A may be adjusted to 6-8 with 50% sodium hydroxide solution.

The modified cation exchange resin is generated as detailed in FIG. 2. Resin A may be a cation exchange resin with similar functionality to Supleco Diaion CR11. Resin A is rinsed with deionized water, then a solution made from copper(II) salts such as copper(II)chloride, copper(II)sulfate, copper(II)nitrate or other copper(II) based species is added to the resin and allowed to interact (Mixture A). The mole ratio of copper to active sites on the resin can range from 0.05:1 to 100:1. The mole ratio of added copper to active sites on resin can be 2:1. The copper solution is then removed and additional deionized water is then used to rinse the resin, forming Resin B. Resin B is loaded into the appropriate vessel (column, cartridge or other container) and used for purification of Solution B, as shown in FIG. 1.

Solution B is exposed to the copper modified (or doped) cation exchange resin (Resin B). This exposure may occur in a vessel in which the resin and NaNT solution are mixed. This exposure may occur in a column containing the copper modified resin through which the NaNT solution is eluted and collected. Additionally, this exposure may occur in a cartridge loaded with copper modified resin, which may be integrated into a continuous flow reaction system. The product of this procedure is collected as purified NaNT solution and is of sufficient purity for subsequent synthesis of DBX-1 primary explosive.

The copper(II) modified resin (Resin B) may be rinsed with copper(II) salt solution or deionized water or a combination of the two to restore purification functionality once the capacity for purification of the resin has been exceeded.

All resin preparation and solution purification processes may be performed in a temperature range between 0-100° C. These processes may be performed between 15-30° C.

Those skilled in the art will appreciate that the specifics of the processes provided may be modified, without departing from the present disclosure.

EXAMPLES

The following examples demonstrate the utility of the present processes.

Example 1

A raw flow NaNT solution (5I072A) was produced by the continuous flow method detailed in U.S. Pat. No. 9,718,791. The solution was treated with 11 volume percent concentrated nitric acid to remove excess nitrite (solution A, 5I085A). The pH of the NaNT solution was raised to approximately 7 with NaOH prior to loading on the column (Solution B, FIG. 1). All processing and purification of the flow NaNT solution was performed at ambient temperature.

Seven hundred and fifty mL of Supelco Diaion CR11 iminodiacetate based cation exchange resin were rinsed with >3 L deionized water (Resin A, FIG. 2). A separate solution of copper(II) chloride dihydrate was prepared at 3.2M copper. The Resin A and 300 mL of the copper solution were combined at a 0.62:1 mole ratio of resin active sites to copper ion. While stirring, the tan resin became blue as the copper solution was added (Mixture A, FIG. 2). The mixture was stirred for 2.5 hrs. The liquid was then decanted off and the solid resin was rinsed >4 L deionized water to afford Resin B, FIG. 2. A volume of 15 mL of the modified resin was then loaded wet into a 25 mL buret (1.2 cm ID) with a stopcock and glass wool plug to prevent resin from escaping. An additional 50 mL of deionized water was passed through the buret to ensure good column packing.

The treated NaNT solution (Solution B, FIG. 1) was added to the head of the column in 10 mL aliquots and passed through the resin bed, affording multiple fractions of purified NaNT solution. The initial 30 mL of effluent from the column was discarded as the concentration of NaNT was low. Previous studies indicated that an initial quantity of NaNT (approximately 0.07 grams per mL of resin) is required to "charge" the column prior to collection of purified product. The remainder of the effluent from this trial was collected for DBX-1 production. The duration of each fraction elution was approximately 5-6 minutes, the pH of the eluting fractions (solutions 5G047 F1-F20) was between 2.9-3.6. HPLC analysis of all fractions was performed to determine the concentration of NaNT, 1H-tetrazole, 5-nitraminotetrazole, and bitetrazoleamine.

TABLE 1

| | Solution | NaNT (M) | Tetrazole (M) | Nitramino Tetrazole (M) | Bitetrazole Amine (M) | Nitrate (M) | Nitrite (M) | pH |
|---|---|---|---|---|---|---|---|---|
| HPLC and IC Analytical Results | | | | | | | | |
| Raw | 5I072A | 0.245 | 0.035 | 0.00028 | 0.00099 | 0.66 | 0.99 | 5.65 |
| Solution A | 5I085A | 0.237 | 0.022 | 0.00019 | 0.00079 | 2.5 | 0.019 | 0.13 |
| Solution B | 5I085B | 0.240 | 0.024 | 0.00018 | 0.00078 | 2.3 | 0.013 | 6.92 |
| Purified | 5I085C Fraction13 | 0.241 | Not Detected | Not Detected | Not Detected | *** | *** | 3.24 |
| Purified | 5I085C Fraction16 | 0.250 | 0.011 | 0.0002 | Not Detected | *** | *** | 3.24 |
| Purified | 5I085C Fraction22 | 0.248 | Not Detected | Not Detected | Not Detected | *** | *** | 3.24 |

Ion Chromatography was not performed on fractions of NaNT solution passed through the purification resin due to copper ion content and incompatibility with the instrument chromatographic column.

Small scale DBX-1 reactions were performed on selected 10 mL fractions of purified NaNT solution (5I085C, fractions 13 and 16) to determine effectiveness of the purification process. It was found that the purification process developed here was effective at preparing up to 130 mL of raw NaNT solution (ca. 5.6 grams NaNT.2H$_2$O) that was of suitable purity to produce DBX-1 from 15 mL of modified resin. An attempt to produce DBX-1 from 5I085C Fraction 16 was unsuccessful. It was thus determined that the capacity of the column had been exceeded.

After the purification capacity of the modified resin had been exceeded, the column was rinsed with 50 mL deionized water, 10 mL of 0.45 M copper(II)chloride dihydrate solution, and 100 mL deionized water. The purification procedure was repeated on additional Solution B. The resin was again effective at purification of solution B, producing purified NaNT solution that was of suitable purity to produce DBX-1 as demonstrated by successful small scale DBX-1 synthesis from NaNT solution 5I085C Fraction 22.

Example 2

A 250 mL aliquot of flow NaNT solution (5I072A) was produced by the continuous flow method detailed in U.S. Pat. No. 9,718,791. The resulting solution was analyzed by HPLC and IC, the components of the solution detected by this methodology are listed in Table 2. In this example, the raw NaNT solution, pH 5.65, was treated with 200 mL wet Dowex Marathon C resin, which had been converted to the acid form by saturation with 8% HCl solution. Gas evolution was observed and continued for >1 hour. The solution was stirred magnetically at ambient temperature for approximately 15 hours. No gas evolution was observed at the conclusion of this time. The purpose of this technique was to remove excess nitrite in the NaNT solution, and it was determined that the nitrite concentration had drastically decreased (Table 2, Solution A). Some dilution of the original solution also occurred on treatment with the wet Dowex resin. The pH of Solution A was adjusted to 7.17 with an aqueous NaOH solution and the resulting Solution B (5I072C) was purified over resin at ambient temperature.

Fifty mL of Supelco Diaion CR11 iminodiacetate based cation exchange resin were rinsed with >1000 mL deionized water and soaked in additional 200 mL deionized water for >5 hours (Resin A). A separate solution of copper(II)chloride dihydrate was prepared by adding >50 mL deionized water to 11.1 grams of CuCl$_2$. The solutions were combined while stirring. The tan resin became blue as the copper solution was added (Mixture A). Mixture A was stirred for >3 hrs. The liquid was decanted off and the solid resin was rinsed with >500 mL deionized water. The modified resin B was then loaded wet into a 100 mL buret (1.5 cm ID) with a stopcock and glass wool plug to prevent resin from escaping. An additional 200 mL of deionized water was passed through the buret to ensure good column packing.

NaNT solution B (5I072C) was added to the head of the column in 100 mL aliquots and passed through the resin bed. The initial 100 mL of effluent from the column was discarded, as the concentration of NaNT was low. Previous studies indicated that an initial quantity of NaNT (approximately 0.07 grams per mL of resin) is required to "charge" the column prior to collection of purified product. The remainder of the effluent from this trial was collected and used for DBX-1 production. The duration of each fraction elution was approximately 40 minutes, the pH of the purified fractions (5I072D) was 3.8. HPLC analysis of 5I072D was performed to determine the concentration of NaNT, 1H-tetrazole, nitraminotetrazole and bitetrazoleamine.

TABLE 2

HPLC and IC Analytical Results

| Solution | NaNT (M) | Tetrazole (M) | Nitramino Tetrazole (M) | Bitetrazole Amine (M) | Nitrate (M) | Nitrite (M) | pH |
|---|---|---|---|---|---|---|---|
| 5I072A | 0.245 | 0.035 | 0.00028 | 0.00099 | 0.65 | 0.99 | 5.7 |
| 5I072B | 0.175 | 0.015 | ND | 0.00042 | 0.66 | 0.008 | 0.6 |
| 5I072C | — | — | — | — | — | — | 7.2 |
| 5I072D | 0.178 | ND | ND | ND | — | — | 3.8 |

Ion Chromatography was not performed on fractions of NaNT solution passed through the purification resin due to copper ion content and incompatibility with the instrument chromatographic column.

A small scale DBX-1 reaction was performed on 5.6 mL of purified NaNT solution 5I072D (fraction 2) to determine effectiveness of the purification process. It was found that the purification process developed here was effective at preparing raw NaNT solution that was of suitable purity to produce DBX-1.

Example 3

A flow NaNT solution was produced by the continuous flow method detailed in U.S. Pat. No. 9,718,791. The solution was treated with nitric acid to remove excess nitrite (Solution A). This solution was then treated with sodium hydroxide to bring the pH up to approximately 7, thereby yielding Solution B. Solution B was analyzed by HPLC and passed through a column for purification. Two columns of differing diameters were utilized. The first column utilized was outlined in Example 2. A total of 3300 mL was passed through this column to afford purified NaNT (5G138) with recharging as needed. A second column was prepared with 450 mL raw Supelco Diaion CR11 iminodiacetate based cation exchange resin, which was rinsed thoroughly (Resin A). A copper(II) chloride dihydrate solution was made by adding 99.6 g $CuCl_2 \cdot 2H_2O$ into 400 mL deionized water and mixing until all the solid was in solution. Resin A was then mixed with this copper solution for two hours (Mixture A). The solution was decanted and rinsed to remove excess copper to afford Resin B. Resin B was then loaded wet into a 1000 mL column (5 cm ID) with a stopcock and glass wool plug to prevent resin from escaping from the bottom of the column. An additional 500 mL of deionized water was passed through the column before allowing 2330 mL of Solution B (5D089G) to pass through the resin in multiple runs with recharging as needed. The effluent was subsequently analyzed by HPLC to ensure the impurities had been removed for DBX-1 synthesis. The two column purified NaNT samples were combined and this solution was used to produce a 100 g batch of DBX-1 via the method outlined in U.S. Pat. No. 8,163,786.

The components before and after treatment are listed in Table 3 below.

TABLE 3

HPLC Analytical Results

| | Solution | NaNT (M) | Tetrazole (M) | Bitetrazole (M) | Nitrate (M) | Nitrite (M) |
|---|---|---|---|---|---|---|
| Soln A | 5D101B 10% | 0.201 | 0.013 | trace | 1.053 | Not Detected |
| Soln B | 5G166 | 0.194 | 0.01 | 0.0002 | 0.844 | Not Detected |
| Purified | 5G138 | 0.187 | Not Detected | Not Detected | 0.891 | Not Detected |
| Raw | 5D089E | 0.183 | 0.008 | Not Detected | 0.8 | 0.019 |
| Soln B | 5D089G | 0.15 | 0.009 | Not Detected | 0.93 | Not Detected |
| Purified | 5G161 | 0.206 | Not Detected | Not Detected | 0.872 | Not Detected |

Different arrangements of the components depicted in the drawings or described above, as well as components and steps not shown or described are possible. Similarly, some features and sub-combinations are useful and may be employed without reference to other features and sub-combinations. For example, the choice of using two different tubing diameters of two different lengths or any combination of tubing diameters and lengths connected together to provide sufficient residence times to complete the conversion of 5-aminotetrazole and nitrite to form 5-nitrotetrazolate is allowable. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A method of purifying a 5-nitrotetrazolate solution comprising:
   treating the 5-nitrotetrazolate solution with a copper(II) modified cation exchange resin.

2. The method of claim 1, wherein the method is performed as a stand-alone system.

3. The method of claim 1, wherein the method is performed as a system integrated into a continuous flow reactor.

4. The method of claim 1, further comprising treating the 5-nitrotetrazolate solution with an acid solution or a resin bound acid prior to treating the 5-nitrotetrazolate solution with the copper(II) modified cation exchange resin.

5. The method of claim 4, further comprising raising a pH of the 5-nitrotetrazolate solution after treating with the acid solution or the resin bound acid.

6. The method of claim 1, further comprising rinsing the copper(II) modified cation exchange resin with at least one of a copper(II) salt solution and deionized water after treating the 5-nitrotetrazolate solution.

* * * * *